United States Patent [19]

Zimmerman et al.

[11] Patent Number: 4,831,118

[45] Date of Patent: May 16, 1989

[54] FLOUROPLASTIC IMMUNOAFFINITY COLUMNS FOR PURIFICATION OF BLOOD PROTEINS

[75] Inventors: Theodore S. Zimmerman; Carol A. Fulcher, both of La Jolla, Calif.

[73] Assignee: Scripps Clinic and Research Foundation, La Jolla, Calif.

[21] Appl. No.: 83,670

[22] Filed: Aug. 7, 1987

[51] Int. Cl.$^4$ .......................... C07K 3/20; C07K 3/18; C07K 17/08; C07K 15/06
[52] U.S. Cl. .................................... 530/383; 530/380; 530/381; 530/387; 530/413; 530/384; 530/389; 530/417; 530/830; 530/815; 530/816; 530/415; 436/532; 436/535; 424/101
[58] Field of Search ............... 530/381, 382, 383, 413, 530/415, 387, 389; 436/532, 535; 424/101, 85

[56] References Cited

U.S. PATENT DOCUMENTS

| | | | |
|---|---|---|---|
| Re. 32,011 | 10/1985 | Zimmerman et al. | 530/383 |
| 4,338,094 | 7/1982 | Elahi | 436/535 |
| 4,361,509 | 11/1982 | Zimmerman et al. | 530/473 |
| 4,657,894 | 4/1987 | Zimmerman et al. | 530/381 |
| 4,689,310 | 8/1987 | Kramer et al. | 436/532 |

FOREIGN PATENT DOCUMENTS

| | | | |
|---|---|---|---|
| 83/02114 | 6/1983 | PCT Int'l Appl. | 424/101 |
| 85/01941 | 5/1985 | PCT Int'l Appl. | 530/381 |

OTHER PUBLICATIONS

Von Klitzing et al, Chem. Abs., 99, 101950j, 1983.
Moskvin et al, Chem. Abs., 82:129731m, 1975.
Hjertén et al, J. Chromatog., 202, 391-5, 1980.
Hjertén, J. Chromatog., 159, 47-55, 1978.

*Primary Examiner*—Margaret Moskowitz
*Assistant Examiner*—Jeff P. Kushan
*Attorney, Agent, or Firm*—Morgan & Finnegan

[57] ABSTRACT

The present invention is a protein purification column comprising an organic substrate matrix having low reactivity to proteins, said matrix being capable of maintaining monoclonal antibodies attached thereto in an external configuration and preventing interaction with the protein to be bound to the antibody, and a monoclonal antibody attached to the substrate, the monoclonal antibody having a specific affinity for the protein to be isolated.

The present invention also is a method for isolating and purifying specific protein from a solution, wherein
1. Protein-specific monoclonal antibody is attached to the organic substrate matrix described above to form an antibody-substrate conjugate; and
2. Protein to be isolated, in an appropriate buffer solution, is contacted with the antibody-substrate conjugate.

An appropriate buffer may be applied to remove non-antibody bound contaminants, followed by an appropriate eluting agent to remove the protein from the monoclonal antibody.

17 Claims, No Drawings"

FLOUROPLASTIC IMMUNOAFFINITY COLUMNS FOR PURIFICATION OF BLOOD PROTEINS

FIELD OF THE INVENTION

The invention relates to an improved protein purification column and method for separating proteins using monoclonal antibodies.

BACKGROUND OF THE INVENTION

Affinity chromatography is commonly used for isolation and separation of proteins in solution. Wilchek et al., "Affinity Chromatography", *Methods in Enzymology*, volume 104, p. 3 (1984) describes conventional supports and activating agents used in affinity chromatography, as well as "newer and effective methods for the preparation and assay of affinity matrices." An adsorbent having a specific affinity for the protein to be isolated is used to biospecifically select the protein. The adsorbent is attached to a support. After the protein solution contacts and binds to the adsorbent, an eluent is added which removes the bound protein from the adsorbent. The resulting solution is highly purified separated protein.

Suitable adsorbents may have general affinity for certain classes of proteins, or specific affinity for proteins having binding sites for the immobilized adsorbent-ligand.

Zimmerman and Fulcher, U.S. Pat. No. Re. 32,011 (hereby incorporated by reference) describe purification of a plasma protein using monoclonal antibodies. Monoclonal antibodies having a specific affinity for a particular protein are prepared and covalently attached to a support such as glass beads, agarose and derivatives thereof. After binding the specific protein to the monoclonal antibody, a washing step removes the protein to produce a highly purified protein solution.

Although the product isolated by Zimmerman et al. is highly purified, there is often a loss of protein in the recovered preparation. The cause of the loss is not known, but one of the causes may be that the support used in protein purification interacts and binds to or internalizes the protein which is to be isolated, and is not removed from the support when eluent is applied to remove protein from the monoclonal antibody. Such interaction may be the result of direct reactivity between the support and protein. It is also thought that antibody which is to be externally bound to the support is instead internalized and rendered useless for isolating protein to which it is specific.

The present invention is a protein purification column comprising an organic substrate matrix having low reactivity to proteins. The matrix is capable of maintaining monoclonal antibodies attached thereto in an external configuration and preventing interaction with the protein to be bound to the antibody, a monoclonal antibody having a specific affinity for the protein to be isolated attached to the substrate, and means for linking the antibody to the substrate.

The present invention also is a method for isolating and purifying specific protein from a solution, wherein 1. Protein-specific monoclonal antibodies are attached to an organic substrate matrix such as that described above to form an antibody-substrate conjugate; and 2. Protein to be isolated, in an appropriate buffer solution, is contacted with the antibody-substrate conjugate.

An appropriate buffer may applied to remove non-antibody bound contaminants followed by an appropriate eluent to remove the protein from the monoclonal antibody.

Protein which fails to bind ("fall-through") to the antibody on initial contact (as described in step 2) can be reapplied after eluting the column.

The substrates may be, for example, fluoroplastic materials such as perfluorinated membrane, perfluoropolymer resin, and perfluorocarbon resin. Sperati, "Fluoroplastics", Modern plastics Encyclopedia 1986-1987, pages 22-25, hereby incorporated by reference, describes these materials in detail.

Perfluorinated membranes are based on perfluorinated ion exchange polymers that provide chemical and thermal stability similar to that of fluorocarbon resin. Attached to the fluoropolymer chains are perfluorinated cation exchange sites. The polymer is permeable to many cations and polar compounds, but impermeable to anions and non-polar species. The membranes are thin polymer films which are usually reinforced with a perfluorocarbon resin support cloth. They are useful as separators. In a typical application, a fluid containing one or more components is in contact with one side of the membrane, and the preferred component is transferred through the membrane under influence of a driving force such as concentration difference across the membrane, electric potential, or hydrostatic pressure. These membranes include sulfonic films, reinforced sulfonic films, and reinforced bimembranes comprised of carboxylic and sulfonic films. Waller and Van Scoyoc, "Catalysis with Nafion", *Chemtech* July 1987, pp. 438-441 describe use of perfluorinated membranes as catalyst support for superacid catalysis "for a wide variety of reactions in synthetic organic chemistry" and for "metal ion exchange."

Perfluorocarbon resins are polymers and copolymers formed from fluorocarbon materials such as tetrafluoroethylene and hexafluoropropylene. Because these materials are resistant to high temperatures and chemically inert to almost all industrial chemicals and solvents, they are widely used to provide corrosion protection in chemical processing equipment by lining pipes, valves, pumps, and vessels. Characteristics of this material are the very strong interatomic bonds between carbon and fluorine atoms, the highly effective shielding of the polymer's carbon backbone by fluorine atoms, and its high molecular weight compared to other polymers.

Perfluoropolymer resins are thermoplastic materials that are highly resistant to attack by chemicals and solvents that cause rapid deterioration of other plastics. These resins are less dense, tougher, stiffer, and exhibit higher tensile strength creep resistance than perfluorocarbon resins.

The art does not teach protein purification columns having substrates as described above. Furthermore, the art does not teach or suggest that monoclonal antibodies suitable for isolating specific proteins can be attached to these types of substrates as described above to provide nearly complete isolation and recovery of a specific protein from a solution containing various other materials.

SUMMARY OF THE INVENTION

The present invention is a protein purification column comprising an organic substrate matrix having low reactivity to proteins, said matrix being capable of maintaining monoclonal antibodies attached thereto in an external configuration and preventing interaction with the protein to be bound to the antibody, a monoclonal antibody having a specific affinity for the protein to be isolated attached to the substrate, and means for linking the antibody to the substrate.

The organic substrate matrix materials are capable of preventing internalization of macromolecules such as antibodies and blood coagulant proteins.

The present invention also is a method for isolating and purifying specific protein from a solution, wherein 1. Protein-specific monoclonal antibody is attached to an organic substrate matrix such as that described above to form an antibody-substrate conjugate; and 2. Protein to be isolated, in an appropriate buffer solution, is contacted with the antibody-substrate conjugate.

An appropriate buffer may be applied to remove non-antibody bound contaminants, followed by an appropriate eluting agent to remove the protein from the monoclonal antibody.

The present invention is also a substrate-antibody-protein conjugate and method for isolating and purifying a protein from a solution comprising an organic substrate matrix as described above, a monoclonal antibody attached to the substrate, and a protein specific to the antibody.

DETAILED DESCRIPTION OF THE INVENTION

Organic substrate matrix materials useful in the present invention include fluoroplastic materials such as perfluorinated membranes, perfluoropolymer resins, and perfluorocarbon resins, which are described above. Characteristic of these materials is that they are chemically stable and do not readily interact with proteins. These materials are sold by Dupont under the trademarks TEFLON®, TEFZEL®, and NAFION®. British Pat. No. 1,184,321 describes perfluorinated membranes. U.S. Pat. No. 3,282,875 describes fluorocarbon vinyl ether polymers. U.S. Pat. Nos. 2,943,080, 2,394,243, and 2,393.967 describe perfluorocarbon resins. Each of these patents are hereby incorporated by reference.

Various proteins which can be isolated using conventional affinity chromatography support materials may be isolated using the column and method of the present invention. In particular, proteins which can be isolated using monoclonal antibody adsorbents may be used. Such proteins include globular proteins, plasma proteins such as coagulants, cell extracts, cofactors, labeled proteins, and enzymes. Recovery of proteins which are particularly difficult to recover because of their attachment to conventional supports can be dramatically increased by using supports such as those described above.

Specific examples of proteins which can be isolated using the column and method of the present invention are factor VIII von Willebrand factor complex (VIII:C-/VIII:RP complex); factor VIII procoagulant activity protein (VIII:C); von Willebrand factor (VIII:RP) (see U.S. Pat. No. Re. 32,011, column 1, lines 35–60); factor IX; vitamin K dependent clotting factors such as X, VII, II, protein C, and protein S; antithrombin III; tissue factor inhibitor; plasminogen activator inhibitor; tissue plasminogen activator; erythropoietin; colony stimulating factors; growth factors; protein C inhibitor; interleukins; labeled proteins; DNA probes; interferons; hepatitis vaccine; lipocordons; or any protein, peptide, or fragment to which a monoclonal antibody can be made or bound. The source of proteins such as VIII:C, VIII:RP and factor IX may be plasma or a recombinant source.

Isolation of factor VIII proteins may be achieved by the usual methods such as those described in U.S. Pat. No. Re. 32,011, with the exception that an organic substrate matrix such as one of those described above is used instead of agarose or other conventional support.

In one embodiment of the invention, factor VIII:C is isolated from the factor VIII von Willebrand factor complex by first cleaving the VIII:C/VIII:RP linkage, binding the VIII:C protein to monoclonal antibody which is specific to VIII:C and which is attached to a perfluorocarbon-based support, and then proceeding according to the procedure described above for isolating the protein.

In another embodiment of the invention, factor VIII von Willebrand factor complex (VIII:C/VIII:RP complex) from a plasma or commercial concentrate source is adsorbed to monoclonal antibody which is specific to VIII:RP and which is attached to a perfluorocarbon-based support. VIII:C is eluted and adsorbed to a monoclonal antibody specific to VIII:C, and then eluted once more to obtain a highly purified and concentrated VIII:C solution.

All of the protein to be isolated and present in solution may be completely attached to the monoclonal antibody provided fluid flow rate is reasonable. If flow rate is too high and insufficient time is allowed for all protein to bind to antibody, the "pass through" fluid may be collected at the end of the column and re-applied through the column to attach the remaining protein. If flow rate is maintained at a relatively low level (such as the rate described in Example 2), most of the protein may be recovered in the eluate rather than the pass-through fluid.

Concentration of antibody can be between about 0.5 mg/ml and about 10 mg/ml, preferably between about 0.5 mg/ml and about 3 mg/ml, and more preferably between about 1.0 mg/ml and 2.0 mg/ml.

Column washing prior to removal of the isolated protein from the antibody can be performed in one step since the support is essentially chemically inert. Elimination of non-antibody bound contaminants is easily achieved.

EXAMPLE 1

Four vials of Armour Factorate concentrate lot 1069B were reconstituted with 15 milliliters of Factor VIII buffer per vial. A total of 62 milliliters was then loaded on a column consisting of 300 milliliters of anti-von Willebrand Factor monoclonal antibody 2.2.9 which had been conjugated at a concentration of approximately 1 mg. monoclonal antibody per ml. The Factor VIII containing column was then washed with 6 column volumes of Factor VIII buffer. All effluent buffer was collected to determine the amount of Factor VIII which did not bind to the column ("pass through"). After assay of the pass through fluid, it was frozen at $-70°$ C. Factor VIII was then eluted from the column with 0.35 M $CaCl_2$. The column was regenerated by elution of the bound von Willebrand Factor with 3M NaSCN. Three and one-half weeks later the frozen pass through was thawed and reapplied to the column. The second pass through fluid was assayed and the bound Factor VIII eluted.

Results

Of the initial 1410 units of Factor VIII applied to the column, 566 were present in the pass through fluid and 704 were eluted for a total recovery of 1270 (recovery was 90%; 50% in the highly purified Factor VIII elute and 40% in the pass through fluid). After thawing, the pass through fluid contained 509 units. When this was applied to the column, 340 units passed through and 163 were eluted in highly purified form. Total recovery for this second run was 99%. Adding the 704 and 163 units eluted in both runs, a total of 865 units, or 61% was recovered in highly purified form. Final total recovery for both runs was 865+340=85%.

EXAMPLE 2

Four vials of Armour Factorate concentrate lot 1069B were reconstituted with 15ml of factor VIII buffer per vial. The vials were pooled and then filtered through 8-10 micron 47 mm AP-25 (Millipore). A total of 59 milliliters were loaded on a column similar to the column used in Example 1 (except that monoclonal antibody was present at a concentration of 2 mg/ml) at 2.2 ml/min., and then washed through the column at 2.3 ml/min. (about 325 ml void volume). The column was subsequently washed over night at 0.7 ml/min. The pass-through fluid and wash was 935 ml.

Factor VIII was then eluted from the column with 0.35 M $CaCl_2$ buffer. The elution rate was 2.5 ml/min., and the following fractions were collected:

| Elution fraction | Volume |
| --- | --- |
| Pre-$CaCl_2$ | 210 ml |
| $CaCl_2$-1 | 100 ml |
| $CaCl_2$-2 | 148 ml |
| $CaCl_2$-3 | 50 ml |
| $CaCl_2$-4 | 50 ml |

$CaCl_2$ fractions 3 and 4 were too slow for accurate determination, so fractions 2, 3 and 4 were pooled and reassayed.

| Fraction | Volume | Time (sec.) | Total Units |
| --- | --- | --- | --- |
| Pool 1069B | 59 ml | 55.8 | 1283 |
| Pass-through fluid and wash | 935 ml | 75.4 | 131 |
| $CaCl_2$-1 | 100 ml | — | — |
| $CaCl_2$-2,3,4 | 250 ml | 55.8 | 1088 |

The data show total protein recovery as 95%, with 85% present in eluate and 10% in the pass-through and wash.

The results in this example indicate not only the high recovery achieved using a column having a perfluorocarbon support, but also the advantages to slowly pumping the protein-containing solution through the column and maintaining a higher concentration of monoclonal antibody. The combination of slowly pumping the solution and increasing the concentration of antibody increased the amount of protein bound to the antibody and recovered in eluate, and decreased that in the pass-through.

Examples 3-8 show results of similar tests using a column such as the one used in Example 1.

EXAMPLES 3-8

| EX-AMPLE | Units Loaded onto Column | Units Passed Through | Units Eluted | Total Units Recovered | % Recovery |
| --- | --- | --- | --- | --- | --- |
| 3 | 3038 | 1356 | 983 | 2339 | 77% |
| 4 | 1350 | 1053 | 344 | 1397 | 103% |
| 5 | 1373 | 997 | 464 | 1461 | 106% |
| 6 | 705 | 544 | 175 | 719 | 102% |
| 7 | 1470 | 955 | 670 | 1625 | 110% |
| 8 | 509 | 340 | 163 | 503 | 99% |

EXAMPLES 9-10

Using the procedure described in Example 1, agarose supports were used instead of perfluorocarbon supports. Total recovery for Example 9 was 48%, and total recovery for Example 10 was 42%. These examples show that % recovery using fluoroplastic supports is greatly superior to % recovery using conventional supports.

EXAMPLE 11

Using the procedure described in Example 1, perfluorinated membrane supports are used instead of perfluorocarbon supports. Excellent protein purification and recovery is achieved.

EXAMPLE 12

Using the procedure described in Example 1, perfluoropolymer resin supports are used instead of perfluorocarbon supports. Excellent protein purification is achieved.

In another embodiment of the invention, a substrate-antibody-protein conjugate is formed by adding to the solution having the protein to be isolated a liquid organic substrate matrix described above having attached to it monoclonal antibody specific to the protein to be isolated. Subsequent to formation of the conjugate, the conjugate settles and remaining liquid is removed. The conjugate is washed to remove non-antibody-bound contaminants, and an eluent is used to remove the protein from the antibody.

What is claimed is:

1. A column for isolating protein comprising:
   (a) a fluoroplastic substrate matrix having low reactivity to proteins, said matrix being capable of maintaining monoclonal antibodies attached thereto in an external configuration and preventing interaction with the protein to be bound to the antibody;
   (b) an monoclonal antibody having a specific affinity for the protein; and
   (c) means for linking said monoclonal antibody to said substrate matrix.

2. A column of claim 1 wherein the matrix is perfluorinated membrane, perfluorocarbon resin, or perfluoropolymer resin.

3. A column of claim 2 wherein the perfluorocarbon resin is polytetrafluoroethylene.

4. A column of claim 2 wherein the perfluorocarbon resin is polyhexafluoropropylene.

5. A column of claim 2 wherein the perfluorinated membrane is a perfluorinated ion exchange polymer having perfluorinated cation exchange sites.

6. A method for isolating protein comprising
(a) forming a column comprising:
   (i) a fluoroplastic substrate matrix having low reactivity to proteins, said matrix being capable of maintaining monoclonal antibodies attached thereto in an external configuration and preventing interaction with the protein to be bound to the antibody;
   (ii) a monoclonal antibody having a specific affinity for the protein; and
   (iii) means for linking said monoclonal antibody to said substrate matrix; and
(b) contacting a buffer solution having the protein to be isolated with the monoclonal antibody to bind the protein to the monoclonal antibody.

7. A method of claim 6 wherein the protein is a plasma protein.

8. A method of claim 6 wherein the protein is a coagulative protein.

9. A method of claim 6 wherein the protein is a recombinant protein.

10. A method of claim 6 wherein the protein is Factor VIII:C.

11. A method of claim 6 wherein the protein is Factor VIII:RP.

12. A method of claim 6 wherein the protein is Factor IX.

13. A method of claim 6 wherein the protein is Factor VIII:C, said factor VIII:C having first been dissociated from Factor VIII:RP prior to step (b).

14. A method of claim 6 wherein the monoclonal antibody is specific to VIII:RP.

15. A method for isolating Factor VIII:C comprising:
(a) forming a column comprising:
   (i) a fluoroplastic substrate matrix having low reactivity to proteins, said matrix being capable of maintaining monoclonal antibodies attached thereto in an external configuration and preventing interaction with the protein to be bound to the antibody;
   (ii) a monoclonal antibody specific to Factor VIII:RP; and
   (iii) means for linking said monoclonal antibody to said substrate matrix;
(b) contacting a buffer solution having a VIII:C-/VIII:RP complex with said monoclonal antibody to bind Factor VIII:RP to the antibody.

16. An improved immunoadsorbent for isolation of coagulation proteins comprising an antibody reactive to said proteins bound to a substrate having low reactivity to said proteins, said substrate being capable of maintaining monoclonal antibodies attached thereto in an external configuration and preventing interaction with the protein to be bound to the antibody.

17. An immunoadsorbent of claim 16 wherein said substrate is a fluoroplastic selected from the group consisting of perfluorinated membrane, perfluorocarbon resin and perfluoropolymer resin.

* * * * *

UNITED STATES PATENT AND TRADEMARK OFFICE
CERTIFICATE OF CORRECTION

PATENT NO. : 4,831,118
DATED : May 16, 1989
INVENTOR(S) : Zimmerman et al.

It is certified that error appears in the above-identified patent and that said Letters Patent is hereby corrected as shown below:

Column 1, line 6, after the title insert --This invention was made with government support under Grant Number HL 35090 and HL 31950 awarded by The National Institute of Health. The government has certain rights to this invention.--

Signed and Sealed this

Twenty-fifth Day of January, 1994

Attest:

BRUCE LEHMAN

*Attesting Officer*     *Commissioner of Patents and Trademarks*